United States Patent [19]

Habig et al.

[11] Patent Number: 5,208,376

[45] Date of Patent: May 4, 1993

[54] PROCESS FOR THE CONTINUOUS PREPARATION OF 3,3'-DICHLORO-BENZIDINE DIHYDROCHLORIDE

[75] Inventors: Kurt Habig, Mörfelden-Walldorf; Konrad Baessler, Frankfurt am Main; Klaus Warning, Eppstein, all of Fed. Rep. of Germany

[73] Assignee: Hoechst Aktiengesellschaft, Frankfurt am Main, Fed. Rep. of Germany

[21] Appl. No.: 856,063

[22] PCT Filed: Nov. 3, 1990

[86] PCT No.: PCT/EP90/01844

§ 371 Date: Jun. 8, 1992

§ 102(e) Date: Jun. 8, 1992

[87] PCT Pub. No.: WO91/07377

PCT Pub. Date: May 30, 1991

[30] Foreign Application Priority Data

Nov. 9, 1989 [DE] Fed. Rep. of Germany ....... 3937320

[51] Int. Cl.$^5$ ............................................ C07C 209/00
[52] U.S. Cl. .................................................... 564/309
[58] Field of Search ......................................... 564/309

[56] References Cited

FOREIGN PATENT DOCUMENTS 0045459 2/1982 European Pat. Off. .
0046185 2/1982 European Pat. Off. .

Primary Examiner—Richard L. Raymond

[57] ABSTRACT

A process for the continuous preparation of 3,3'-dichlorobenzidine dihydrochloride from 2,2'-dichlorohydrazobenzene by treatment with aqueous sulfuric acid, which comprises treating the 2,2'-dichlorohydrazobenzene, dissolved in a water-immiscible aromatic solvent, continuously at temperatures of from about 20° to about 50° C. in the presence of an alkali metal salt of an alkyl ($C_8$–$C_{23}$)polyglycol ether sulfate, with such an amount of from about 50 to about 80 % strength aqueous sulfuric acid that the suspension formed remains conveyable, subsequently diluting the suspension emerging from the reaction zone with water, again continuously, and subsequently heating the suspension to a temperature of from about 90° to about 95° C. until a solution is obtained, separating off the aromatic solvent from the hot, sulfuric acid aqueous phase, and precipitating the 3,3'-dichlorobenzidine dihydrochloride by adding hydrochloric acid to the sulfuric acid solution which remains and filtering off this product.

17 Claims, No Drawings

PROCESS FOR THE CONTINUOUS PREPARATION OF 3,3'-DICHLORO-BENZIDINE DIHYDROCHLORIDE

DESCRIPTION

The invention relates to a process for the continuous preparation of 3,3'-dichlorobenzidine dihydrochloride from 2,2'-dichlorohydrazobenzene by treatment with aqueous sulfuric acid in the presence of an alkali metal salt of an alkyl polyglycol ether sulfate.

3,3'-Dichlorobenzidine has the greatest economic importance of all known diphenyl bases. Both the free base and, in particular, the salts formed with mineral acids are valuable starting materials, for example for the synthesis of dyes.

3,3'-Dichlorobenzidine is usually prepared from 1-chloro-2-nitrobenzene by reduction and subsequent so-called benzidine rearrangement of the resultant 2,2'-dichlorohydrazobenzene. The rearrangement is catalyzed by mineral acid. To this end, the 2,2'-dichlorohydrazobenzene is expediently dissolved in an aromatic solvent, and aqueous mineral acid is then added. The rearrangement then occurs in the aqueous phase, the resultant 3,3'-dichlorobenzidine salt causing the formation of a suspension. With the increasing reaction duration, the viscosity of the suspension increases so much that it is virtually impossible to stir or pump. This furthermore has the consequence that material exchange can only take place by diffusion, and a long reaction time is therefore necessary for complete conversion. Undesired side reactions, such as, for example, disproportionation, thus increase in importance. The by-products reduce the yield of 3,3'-dichlorobenzidine and, in addition, must be removed by complex purification operations.

Usually, exactly the amount of mineral acid required for the reaction is employed in order to keep the work-up costs as low as possible.

EP-A 0 045 459 describes a continuous process for the preparation of diphenyl bases and the salts formed therefrom with mineral acids from the corresponding N,N'-diarylhydrazines. The solution of the hydrazo compound in a water-immiscible aromatic solvent is admixed continuously with such an amount of mineral acid that the suspension remains conveyable. Suitable solvents in this process are all liquid aromatics which have sufficient solvency and are inert under the reaction conditions toward the substances participating in the reaction. Of industrial importance are, in particular, toluene, the isomeric xylenes and the commercially available m-xylene/ethylbenzene mixture, known as "Solvent Naphtha".

In the process of EP-A 0 045 459, the mineral acids used are from 20 to 80 % strength aqueous sulfuric acid or from 10 to 30 % strength aqueous hydrochloric acid. These acids are added in a 10- to 14-fold excess above the amount necessary for salt formation. The reaction is carried out at a temperature of from 20° to 50° C. The volume and design of the reaction zone is determined by the residence time necessary for the reaction mixture. The residence time itself depends on the constitution of the N,N'-diarylhydrazine and on the reaction temperature. At a residence time of from 1 to 3 hours, a cascade of at most 5 stirred reactors has proved advantageous.

The reaction mixture is then worked up in a conventional manner, for example by removing the aromatic solvent by distillation or by blowing through steam and separating the aqueous acid from the precipitated salt of the diphenyl base by filtration, and recycling the aromatic solvent and the aqueous acid, which is concentrated to the original acid content.

It is stated that a particular advantage of the process is that the salts of the diphenyl base are obtained in high yields and at high throughput with a minimum of operations, it being possible to fully recycle the assistants employed into the process.

However, to prepare the pure salts of the diphenyl bases, the crude salt initially produced must be purified either via the free base or by recrystallization from hydrochloric acid.

Although the process of EP-A 0 045 459 has provided a considerable advance, the space-time yields which can be achieved therewith no longer satisfy current requirements. In addition, in the continuous reaction of 2,2'-dichlorohydrazobenzene with aqueous sulfuric acid by this process, unforeseeable changes in viscosity occur, resulting in it being virtually impossible to stir or transfer the suspension. Hitherto, the toluene has been removed from the suspension formed in the reaction of 2,2'-dichlorohydrazobenzene with aqueous hydrochloric acid by distillation in a thin-film evaporator, some of the hydrochloric acid also being removed by azeotropic distillation. In spite of the high costs involved in providing equipment to ensure that no problems occur in a continuous procedure, problems during the process, for example due to difficulties on flowing through the evaporator, cannot always be avoided.

The present invention now provides a continuous process for the preparation of 3,3'-dichlorobenzidine dihydrochloride in which the abovementioned disadvantages of the known process no longer occur.

The process according to the invention for the continuous preparation of 3,3'-dichlorobenzidine dihydrochloride from 2,2'-dichlorohydrazobenzene by treatment with aqueous sulfuric acid comprises treating the 2,2'-dichlorohydrazobenzene, dissolved in a water-immiscible aromatic solvent, continuously at temperatures of from about 20° to about 50° C., preferably from about 36° to about 40° C., in the presence of an alkali metal salt, preferably the sodium salt of an alkyl ($C_8$–$C_{23}$)polyglycol ether sulfate, with such an amount of from about 50 to about 80 % strength, preferably from about 60 to about 65 % strength, aqueous sulfuric acid that the suspension formed remains conveyable, subsequently diluting the suspension emerging from the reaction zone with water, again continuously, and subsequently heating the suspension to a temperature of from about 90° to about 95° C. until a solution is obtained, separating off the aromatic solvent from the hot, sulfuric acid aqueous phase, and precipitating the 3,3'-dichlorobenzidine dihydrochloride by adding hydrochloric acid to the sulfuric acid solution which remains, and filtering off this product.

Examples of suitable water-immiscible aromatic solvents are toluene, the isomeric xylenes, o-dichlorobenzene or solvent mixtures, such as "Solvent Naphtha" (mixture of m-xylene and ethylbenzene), or mixtures thereof.

For the rearrangement reaction, from about 6 to about 7 mol of $H_2SO_4$ are expediently employed per mol of 2,2'-dichlorohydrazobenzene.

The dilution of the suspension emerging from the reaction zone with water is expediently continued until the aqueous phase contains about 40 % by weight of $H_2SO_4$.

The addition of the hydrochloric acid to the sulfuric acid aqueous phase is carried out continuously at temperatures of from about 95° to about 110° C., from about 1.5 to about 2.5 times the amount of hydrochloric acid necessary for salt formation being added. When the addition of hydrochloric acid is complete, the aqueous phase is cooled to from about 30° to about 35° C., and the precipitated 3,3'-dichlorobenzidine dihydrochloride is subsequently filtered off and washed with hydrochloric acid until the acid washings are free from sulfuric acid.

The aromatic solvent can easily be separated off and reused after a re-distillation. After an addition of the aqueous hydrochloric acid, expediently from about 10 to about 35 percent strength by weight, preferably about 30 percent strength by weight aqueous hydrochloric acid, to the hot solution containing 3,3'-dichlorobenzidine sulfate, this aqueous phase being cooled to from about 30° to 35° C., pure, crystalline 3,3'-dichlorobenzidine hydrochloride deposits and can be filtered off without complications and washed with a little hydrochloric acid until free from sulfuric acid. The mineral acid produced can be worked up by conventional methods, such as, for example, those described by Bertrams or Schott, and then re-used. Thus, the process does not involve isolation of an intermediate and is therefore economically and ecologically advantageous. The present process uses an approximately 62 % strength aqueous sulfuric acid at a theoretical residence time of only about 1 hour and only an approximately 6.1-fold molar excess of sulfuric acid, based on 2,2'-dichlorohydrazobenzene.

Compared with the prior art, as expressed in EP-A 0 045 459, this means that the amount of sulfuric acid employed is more than halved and the space-time yield is substantially increased.

The following is observed if the rearrangement is carried out in the absence of an alkali metal salt of an alkyl ($C_8$–$C_{23}$)polyglycol ether sulfate.

In an experimental apparatus comprising 3 consecutive stirred reactors, a steady state can be maintained for about 10 hours without difficulty. Under steady state conditions, at a reaction temperature of from 36° to 40° C., 88 % of the 2,2'-dichlorohydrazobenzene have reacted on leaving the first stirred reactor and 97 % have reacted on leaving the second reactor. No starting material is detectable on entering the third reactor, and the conversion is therefore complete.

After the steady state conditions have been maintained for from 15 to 20 hours, the flow properties of the reaction mixture worsen, unpredictably, and complete blockage of the tube lines occurs, and the experiment must be terminated. The microscopic image now shows microcrystals instead of the rod-like crystals predominating hitherto. In macroscopic terms, this transition is evident from a brightening.

If it has been attempted to extend the duration of the initially achieved steady state by varying the reaction parameters, inter alia increasing the throughput by 25 %, increasing the amount of sulfuric acid by 10 %, reducing the concentration of 2,2'-dichlorohydrazobenzene from 24 to 16 %, increasing the stirring frequency by 20 % and by using another type of stirrer, it is apparent that none of these measures allows the desired effect to be achieved. Even adding emulsifiers based on alkyl polyglycol ethers, organic phosphates or alkylbenzene sulfonates cannot prevent the described transition to the interfering microcrystals.

However, if the process is carried out in the presence of an alkali metal salt of an alkyl ($C_8$–$C_{23}$)polyglycol ether sulfate, the steady state is surprisingly retained during the continuous process procedure.

The alkali metal salts of an alkyl ($C_8$–$C_{23}$)polyglycol ether sulfate, preferably the sodium salts thereof, particularly preferably $C_{12}H_{25}$—O—$(C_2H_4$—$O)_{1-4}$—$SO_3Na$, are effective here in a concentration of from about 0.04 to about 1.0 % by weight, preferably from about 0.1 to about 0.4 % by weight, based on the weight of the reaction mixture. They can be admixed with the sulfuric acid to be added in the form of aqueous solutions or metered in separately to the contents of the first stirred reactor. By carrying out the rearrangement in the presence of an alkali metal salt of an alkyl ($C_8$–$C_{23}$)polyglycol ether sulfate, a steady state can be obtained for the duration of the continuous process.

EXAMPLE

Reaction apparatus:

Cascades comprising 3 stirred reactors of equal volume, each provided with a cooling jacket and a coil or impeller stirrer (300 rpm). Total reaction volume 2.8 l. All the stirred reactors are connected to one another via dip tubes. The starting components are metered continuously into the first stirred reactor under the liquid surface.

Theoretical residence time: 60 min.

Throughput per hour:

407 g of 2,2'-dichlorohydrazobenzene: 1660 g 1253 g of Solvent Naphtha: (1750 ml)

1550 g (1000 ml) of 62 % strength aqueous sulfuric acid 50 g (50 ml) of a 3 % aqueous solution of $$C_{12}H_{25}\text{—O—}(C_2H_4O\text{—})_2\text{—SO}_3Na$$

Reaction temperature: 36° to 40° C.

In the absence of the alkyl polyglycol ether sulfate, the crystal structure of the 3,3'-dichlorobenzidine sulfate changes at the latest within 15 to 20 hours of continuous operation, this change being apparent from a total blockage of all the tube lines. By contrast, the coarse-crystalline modification is stabilized in the presence of an alkyl ($C_8$–$C_{23}$)polyglycol ether sulfate, ensuring uninterrupted continuous operation.

The conversion of the 3,3'-dichlorobenzidine sulphate into 3,3'-dichlorobenzidine dihydrochloride is included in the continuous operation. To this end, the suspension emerging from the third stirred reactor is treated with 840 g of water per hour and then heated to from 90° to 95° C., during which dissolution occurs. The aromatic phase can then easily be separated off and is re-used after distillation. After addition of about 30 % strength aqueous hydrochloric acid to the hot sulfuric acid solution which remains (temperature 95°–110° C.), pure, crystalline 3,3'-dichlorobenzidine dihydrochloride precipitates on cooling, and is filtered off and washed with hydrochloric acid until free from sulfuric acid.

The yield of 3,3'-dichlorobenzidine dihydrochloride is at least 80 % of theory, based on 1-chloro-2-nitrobenzene, or from 88 to 89 % of theory, based on 2,2'-dichlorohydrazobenzene.

Residual moisture: 6 to 8 % by weight.

Diazo value: 77.8 %, based on the free base (dried dichlorohydrate).

The excess mineral acid produced can be worked up again by known methods, for example by those of Bertrams and Schott, and re-used.

If the 1253 g of Solvent Naphtha are replaced by the same amount by weight of o-, m- or p-xylene or o-dichlorobenzene and the procedure is otherwise as in the example, virtually the same result is obtained.

We claim:

1. A process for the continuous preparation of 3,3'-dichlorobenzidine dihydrochloride from 2,2'-dichlorohydrazobenzene by treatment with aqueous sulfuric acid, which comprises treating the 2,2'-dichlorohydrazobenzene, dissolved in a water-immiscible aromatic solvent, continuously at temperatures of from about 20° to about 50° C in the presence of an alkali metal salt of an alkyl ($C_8$–$C_{23}$)polyglycol ether sulfate, with such an amount of from about 50 to about 80 % strength aqueous sulfuric acid that the suspension formed remains conveyable, subsequently diluting the suspension emerging from the reaction zone with water, again continuously, and subsequently heating the suspension to a temperature of from about 90° to about 95° C. until a solution is obtained, separating off the aromatic solvent from the hot, sulfuric acid aqueous phase, and precipitating the 3,3'-dichlorobenzidine dihydrochloride by adding hydrochloric acid to the sulfuric acid solution which remains, and filtering off this product.

2. The process as claimed in claim 1, carried out in the presence of the sodium salt of alkyl ($C_8$–$C_{23}$)—O—($C_2H_4$—O)$_{1-4}$—SO$_3$H.

3. The process as claimed in claim 1 carried out in the presence of the sodium salt of ($C_{12}H_{25}$)—O—($C_2H_4$O)$_2$—SO$_3$H.

4. The process as claimed in claim 1 carried out using from about 60 to about 65% strength aqueous sulfuric acid.

5. The process as claimed in claim 1 wherein from about 6 to about 7 mol of sulfuric acid are employed per mol of 2,2'-dichlorohydrazobenzene.

6. The process as claimed in claim 1, wherein the treatment with aqueous sulfuric acid is carried out at a temperature from about 36° to about 40° C.

7. The process as claimed in claim 1, wherein the aromatic solvent used is toluene, an isomeric xylene, o-dichlorobenzene or Solvent Naphtha, or a mixture thereof.

8. The process as claimed in claim 1, wherein the suspension emerging from the reaction zone is diluted with water until the aqueous phase contains about 40 % by weight of sulfuric acid and is subsequently heated to from about 90° to about 95° C. until a solution is obtained.

9. The process as claimed in claim 1, wherein the hydrochloric acid is added continuously to the sulfuric acid aqueous phase at a temperature of from about 95° to about 110° C.

10. The process as claimed in claim 1, wherein from about 1.5 to about 2.5 times the amount of hydrochloric acid necessary for salt formation is added to the sulfuric acid aqueous phase.

11. The process as claimed in claim 1, wherein from about 10 to about 35 % strength by weight aqueous hydrochloric acid is added to the sulfuric acid aqueous phase.

12. The process as claimed in claim 1, wherein the aqueous phase is cooled to from about 30° to about 35° C. after the hydrochloric acid has been added, and the precipitated 3,3'-dichlorobenzidine dihydrochloride is subsequently filtered off and then washed with hydrochloric acid until the acid washings are free from sulfuric acid.

13. The process as claimed in claim 1, carried out in the presence of a concentration of from about 0.04 to about 1.0 % by weight of the alkali metal salt of the alkyl ($C_8$–$C_{23}$)polyglycol ether sulfate, based on the weight of the reaction mixture.

14. The process as claimed in claim 1, carried out in the presence of a concentration of from about 0.1 to about 0.4 % by weight of the alkali metal salt of the alkyl ($C_8$–$C_{23}$)polyglycol ether sulfate, based on the weight of the reaction mixture.

15. The process as claimed in claim 1, wherein the excess acid is worked up again after separation and is re-used.

16. A continuous process for the preparation of 3,3'-dichlorobenzidine dihydrochloride from 2,2'-dichlorohydrazobenzene by treatment with aqueous sulfuric acid, which comprises:

in a reaction zone from which a product of a reaction can be conveyed, continuously reacting the 2,2'-dichlorohydrozobenzene, dissolved in a water-immiscible aromatic solvent, at a temperature within the range of about 20° to about 50° C. in the presence of an alkali metal salt of a $C_8$–$C_{23}$ alkyl polyglycol ether sulfate, with such an amount of from about 50 to about 80% strength aqueous sulfuric acid that a conveyable suspension containing 3,3'-dichlorobenzidine sulfate is formed in said reaction zone, conveying said conveyable suspension from the reaction zone, continuously diluting the suspension conveyed from the reaction zone with water, heating the thus-diluted suspension to a temperature in the range of from about 90° to about 95° C. until a solution comprising ahot, sulfuric acid aqueous phase is obtained, the aromatic solvent being separable from said solution, separating off the aromatic solvent from the hot, sulfuric acid phase, and precipitating the 3,3'-dichlorobenzidine dihydrochloride by adding hydrochloric acid to the thus-separated sulfuric acid phase, and filtering off said 3,3'-dichlorobenzidine dihydrochloride.

17. The process as claimed in claim 16, wherein the amount of $C_8$–$C_{23}$ alkyl polyglycol ether is selected to insure the continuous formation of a substantially stable coarse crystalline modification of 3,3'-dichlorobenzidine sulfate in the reaction zone, and wherein said continuous process is carried out in a substantially uninterrupted manner for more than 20 hours.

* * * * *

UNITED STATES PATENT AND TRADEMARK OFFICE
CERTIFICATE OF CORRECTION

PATENT NO. : 5,208,376
DATED : May 4, 1993
INVENTOR(S) : Kurt Habig, Konrad Baessler adn Klaus Warning It is certified that error appears in the above-indentified patent and that said Letters Patent is hereby corrected as shown below:

In claim 16, column 6, lime 46, "ahot" should read --a hot--.

Signed and Sealed this

Third Day of May, 1994

Attest:

BRUCE LEHMAN

*Attesting Officer*     *Commissioner of Patents and Trademarks*